(12) United States Patent
Shiba

(10) Patent No.: US 6,356,300 B1
(45) Date of Patent: Mar. 12, 2002

(54) AUTOMATIC VISUAL INSPECTION APPARATUS AUTOMATIC VISUAL INSPECTION METHOD AND RECORDING MEDIUM HAVING RECORDED AN AUTOMATIC VISUAL INSPECTION PROGRAM

(75) Inventor: Hisashi Shiba, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/232,689

(22) Filed: Jan. 19, 1999

(30) Foreign Application Priority Data

Jan. 16, 1998 (JP) .......................................... 10-006552

(51) Int. Cl.$^7$ ............................. H04N 7/18; H04N 9/47
(52) U.S. Cl. ......................... 348/130; 348/95; 382/151
(58) Field of Search ........................... 348/92, 95, 125, 348/129, 130, 126; 356/392, 237.4, 237.5; 382/141, 145, 151, 173, 177, 190, 192, 193, 194, 199, 203, 204; H04N 7/18, 9/47

(56) References Cited

U.S. PATENT DOCUMENTS

| | | | |
|---|---|---|---|
| 4,148,065 A | 4/1979 | Nakagawa et al. | 348/129 |
| 4,805,123 A | 2/1989 | Speecht et al. | 364/559 |
| 5,048,094 A | 9/1991 | Aoyama et al. | 382/151 |
| 5,153,444 A | 10/1992 | Maeda et al. | 250/559.05 |
| 5,574,800 A | 11/1996 | Inoue et al. | 382/149 |
| 6,031,931 A * | 2/2000 | Chiu et al. | 382/199 |
| 6,061,476 A * | 5/2000 | Nichani | 382/145 |
| 6,201,892 B1 * | 3/2001 | Ludlow et al. | 348/126 |

FOREIGN PATENT DOCUMENTS

| | | |
|---|---|---|
| JP | 1-296142 | 11/1989 |
| JP | 3-19990 | 3/1991 |
| JP | 3-76402 | 12/1991 |
| JP | 4-109647 | 4/1992 |
| JP | 4-198741 | 7/1992 |
| JP | 7-63691 | 3/1995 |
| JP | 7-77495 | 3/1995 |
| JP | 8-189902 | 7/1996 |

\* cited by examiner

Primary Examiner—Nhon T Diep
(74) Attorney, Agent, or Firm—Foley & Lardner

(57) ABSTRACT

An image differential unit differentiates an inspection image and a reference image on an object to be inspected. An image division unit divides an image into a predetermined number of divisions. Pixel precision position alignment unit overlays the inspection image and the reference image by carrying out the position alignment in pixel precision which is a pixel size precision. Function fitting unit detects an edge, and obtains intensity profile of the absolute pixel value in the direction orthogonal with the edge, and fits a predetermined single peak function to it. Sub-pixel precision position displacement computing unit computes a difference of the corresponding edge positions as the sub-pixel precision position displacement. Adjusted differential image forming unit forms the adjusted differential image by rewriting the pixel value so that the intensity profile of the pixel value in the direction orthogonal with the edge should follow the single peak type function form on the corresponding two edges. An image comparison unit detects the defect of the object to be inspected by comparing the adjusted divisional differential image of the inspected image with the adjusted divisional differential image of the reference image based on the position displacement of the sub-pixel precision.

8 Claims, 14 Drawing Sheets

EDGE ON REFERENCE IMAGE
EDGE ON INSPECTION IMAGE

DIRECTION VERTICAL TO THE EDGE
EDGE ON INSPECTION IMAGE

AUTOMATIC VISUAL INSPECTION APPARATUS AUTOMATIC VISUAL INSPECTION METHOD AND RECORDING MEDIUM HAVING RECORDED AN AUTOMATIC VISUAL INSPECTION PROGRAM

BACKGROUND OF THE INVENTION

1. Field of the Invention

The present invention relates to an automatic visual inspection apparatus, an automatic visual inspection method and a recording medium having recorded the automatic visual inspection program. More particularly, the invention relates to an automatic visual inspection technique adapted for the purpose of detecting the shape defect of the pattern in the photomask or reticule for lithography of a semiconductor device.

2. Description of the Related Art

In general, in the inspection step in the semiconductor manufacturing, the shape defect of the pattern in the photomask or reticule for lithography of a semiconductor device is inspected by using an image.

As the representative procedures for detecting the shape defect of the pattern by using an image, there are die-to-die system for making comparison by the adjacent chip and the template matting and the die to database system for forming a reference image by the CAD data and making comparison with it, as disclosed in U.S. Pat. No. 4,805,123, Feb. 14, 1989 of Donald F. Specht et al., "Automatic Photomask and Reticle Inspection Method and Apparatus including Improved Defect Detector and Alignment Sub-Systems". As these procedures are simple and relatively small calculation amount, similar procedures are adopted in various automatic visual inspection apparatuses.

Japanese Patent Application Laid-Open No. 7-63691 discloses a pattern defect inspection method and its apparatus for detecting the pattern defect of the member to be inspected by detecting an edge direction in the reference image data for detecting the pattern defect of the an object to be inspected, applying the differential processing respectively to the reference image data and the inspection image data obtained by picking up the image of the object to be inspected according to the edge direction, comparing the reference image data which has been subjected to the differential processing and the inspection image data, and detecting the pattern defect from the difference of the image data between them.

According to the procedure of Donald F. Specht et al., when, for example, there is a defect of lacking in a corner in the inspection image as shown in FIG. 1, alignment is carried out by a template matching with the reference image of FIG. 1B, there may be a case where the images are overlaid together to make the edge parts agree as in FIG. 1C and a case where the images are overlaid together with the edge parts displaced as in FIG. 1D. In a case that the images are overlaid together with full agreement of the edge parts, the difference of the two images are only in the corner in which the defect actually exists, and no false defect occurs. However, when the images are overlaid with displacement of the edge parts as in FIG. 1D, false defects occur in the edge part.

Further, as shown in FIG. 2A (a graph showing the variation of intensity of the image to be inspected) and in FIG. 2B (a graph showing the variation of intensity of the reference image), in a case that the variation of the intensity of the edge part differs between the inspection image and the reference image due to the difference of manufacturing step or image pickup conditions, a false defect occurs in making comparison between the two images as shown in FIG. 2C.

Furthermore, as shown in FIG. 3A (a graph showing the variation of intensity of the image to be inspected) and in FIG. 3B (a graph showing the variation of intensity of the reference image), in a case that a difference arises in the size of offset between the image to be inspected and the reference image, or, as shown in FIG. 4A (a graph showing the variation of intensity of the image to be inspected) and in FIG. 4B (a graph showing the variation of intensity of the reference image), in a case that a difference occurs in the intensity under effect of the difference of gains of the detector or the intensity of the light source, there occurs a false defect.

Furthermore, according to the procedure of Donald F. Specht, et. al., in aligning the positions of the images to be compared, a intensity between the pixels is interpolated to one image to form an image with displacement of a sub-pixel in position, and alignment of a sub-pixel precision was made. Because of this, in a case that of making alignment in high precision, it is necessary to produce a large quantity of the images having delicate degrees of the position displacements for comparison, so that there has been a problem to require an enormous amount of calculations and memory capacity for the purpose.

On the other hand, according to the pattern defect inspection method and its apparatus as disclosed in Japanese Patent Application Laid-Open No. 7-673691, it is told that, even if there are some displacements of coordinates between the coordinate of the inspection image data of the inspection pattern and the reference image data of the reference pattern, it is possible to prevent generation of false defect and to detect securely the pattern defect only. However, the publication does not show the technical matters corresponding to the present invention as to the method of alignment of the images nor any description suggestive of it.

SUMMARY OF THE INVENTION

An object of the present invention is to provide an automatic visual inspection apparatus, an automatic visual inspection method and a recording medium having recorded the automatic visual inspection program with which generation of false defect is prevented and there is no increase in the necessary calculation amount or memory capacity even when the precision of alignment is elevated.

In the automatic visual inspection apparatus of the present invention, an image division differential unit inputs an inspection image on the object to be inspected and a reference image for making comparison with the inspection image, and spatially differentiating the respective inputted images and dividing them into the predetermined number of divisions to form the divisional differential images. A pixel precision alignment unit overlays the inspection image on the reference image by carrying out the position alignment in pixel precision which is a pixel size precision between the inspection image and the reference image on each of the divisional differential image formed by the image division differential unit. A function fitting unit regards the point where the absolute pixel value is larger than the predetermined threshold value to be an edge in each divisional differential image, obtaining the direction of the edge, obtaining the distribution of the intensity of the absolute pixel value in the direction orthogonal with the edge, fitting a predetermined single peak function to it, obtaining the maximum value point which is a coordinate of the point where its function takes the maximum value by a sub-pixel precision which is the precision lower than the pixel size, and employing the resulting value as coordinate of an edge. A sub-pixel precision position displacement computing unit obtains a position displacement of the sub-pixel precision. After the laying over of the images together in the pixel precision position aligning unit, if, there is an edge in the region on the reference image corresponding to the neighborhood of the edge, these two edges are regarded as being in the corresponding relations, and said sub-pixel precision position displacement computing unit computes the difference of the mutual edge positions as a position displacement of the sub-pixel precision. An adjusted differential image forming unit forms the adjusted differential image by rewriting the pixel value so that the intensity profile of the pixel value in the direction orthogonal with the edge should follow the previously given single peak type function form on the corresponding two edges. An image comparison unit detects the defect of the object to be inspected by comparing the adjusted divisional differential image of the inspected image with the adjusted divisional differential image of the reference image based on the position displacement of the sub-pixel precision of each divisional differential image computed by the sub-pixel precision position displacement computing unit.

The above sub-pixel precision position displacement computing unit may compute the average value of the position displacement in sub-pixel precision in all edges in one divisional differential image as the position displacement of the sub-pixel precision of the divisional differential image.

The above image comparison unit may obtain the absolute pixel value showing the difference between the adjusted divisional differential image of the inspection image and the adjusted divisional differential image of the reference image, and in a case that the resulting value exceeds the predetermined threshold value, the unit regards the result to be the defect of the inspected object.

The above image comparison unit may form the adjusted divisional differential image having the position displacement by a sub-pixel by interpolating the intensity between the pixels in either one of the adjusted divisional differential image, and compare it with the other adjusted differential image.

The above sub-pixel precision position displacement computing unit may detect a corner on the divisional differential image, and if a corner exists, the unit effect laying over the images in the pixel precision position alignment unit, after which, if, with respect to the certain corner on the inspected image, there is a corner in the region on the reference image corresponding to the nearest part to the corner, these two corners are regarded to be in corresponding relations, and the difference of the mutual corner positions may be computed as the position displacement of the sub-pixel precision between the corners.

The automatic visual inspection method of the present invention has the following steps.

(1) an inspection image on the object to be inspected and a reference image for making comparison with the inspection image are inputted, and the respective inputted images are spatially differentiated to form the differentiated images;

(2) according to the predetermined number of divisions, the formed differential images and forming the divisional differential images are divided;

(3) the inspection image on the reference image by carrying out the position alignment in pixel precision which is a pixel size precision between the inspection image and the reference image on each formed divisional differential image are overlaid;

(4) in each divisional differential image, the point where the absolute pixel value is larger than the predetermined threshold value to is regarded to be an edge in each divisional differential image; the direction of the edge is obtained; distribution of the intensity of the absolute pixel value is obtained in the direction orthogonal with the edge; a predetermined single peak function is fitted to it; the maximum value point which is a coordinate of the point where its function takes the maximum value is obtained by a sub-pixel precision which is the precision lower than the pixel size; and the resulting value is employed as coordinate of an edge;

(5) after the mutual laying over of the images, if, on certain edge on the inspection image, there is an edge in the region on the reference image corresponding to the neighborhood of the edge, these two edges are regarded as being in the corresponding relations, and the difference of the mutual edge positions is computed as a position displacement of the sub-pixel precision;

(6) an adjusted differential image is formed by rewriting the pixel value so that the intensity profile of the pixel value in the direction orthogonal with the edge should follow the previously given single peak type function form on the corresponding two edges;

(7) the defect of the object to be inspected is detected by comparing the adjusted divisional differential image of the inspected image with the adjusted divisional differential image of the reference image based on the position displacement of the sub-pixel precision of each divisional differential image computed.

The automatic visual inspection method of the present invention may be performed by replacing the sequence of the above step (1) and step (2) such that the input image is divided first and then differentiated to form a divisional differential image.

The recording medium of the present invention is characterized by having recorded a program for causing a computer to execute said method.

The present invention having the constitution as described above has the following effects:

(1) In the present invention, the edge position is detected in the sub-pixel precision, and the inspection image and the reference image which are to be compared based on the detected edge position are position aligned in sub-pixel precision, and in comparing the images after alignment, the intensity profile of the corresponding edges are modified into the same shape.

Accordingly, because of the position alignment made between the edges, even when defects exist in a corner part, there is less tendency for false defect to occur in the edge part in the vicinity of the corner part.

Further, in the differential images to be compared, the intensity profile of the corresponding edge portions are modified into the same shape, so that even if the intensity gradients in the vicinity of the edges differ between the images to be compared, a false defect is less caused to occur.

Moreover, since the offset which is a DC component in image is lost by differentiation, a false defect is less caused to occur even when the offsets differ between the images to be compared.

Furthermore, since the intensity profile of the corresponding edge portions is modified into the same shape, even if the gains of the detector or the intensity of illumination differ between the images, false defects are less caused to occur.

Also, in a case of comparing the edge images, even if the real edge positions differ by about the sub-pixel, usually the difference on the edge image becomes more than one pixel to become the cause for the false defect. However, in a case of comparing the modified images following the given function forms as in the present invention, even if the edge positions of the sub-pixels differ, due to the small difference of the pixel values, a false defect is less caused to occur.

As reviewed above, since in the present invention generation of the false defects can be prevented, highly reliable automatic visual inspection can be carried out.

(2) In the present invention, due to, the computation of the position displacement of the sub-pixel precision on each divisional differential image by obtaining the distance of the corresponding edges between the images to be compared, there is no necessity to make comparison by forming a magnified images. Accordingly, even if the precision of position alignment is elevated, no increase in the necessary calculation amount or memory capacity is required.

DESCRIPTION OF THE PREFERRED EMBODIMENT

Figure 6:
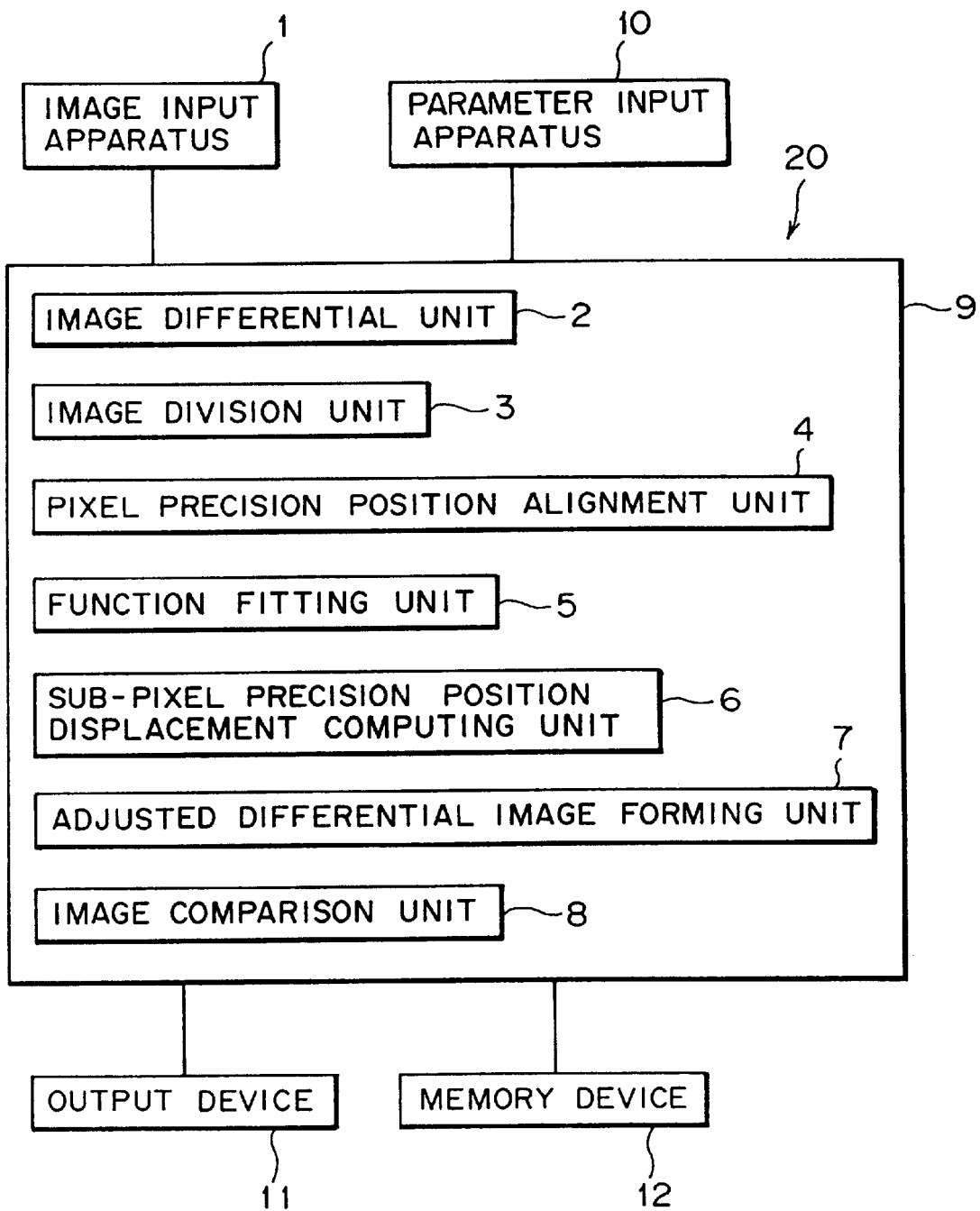
FIG. 6 is a block diagram showing the constitution of the first and the second embodiments of the present invention.

Hereinafter, preferred embodiments of the present invention are described with reference to the appended drawings. FIG. 6 is a block diagram showing an automatic visual inspection apparatus according to the embodiment of the present invention.

The automatic visual inspection apparatus 20 of this embodiment invention is used to detect the pattern shape defect of an object to be inspected (e.g., semiconductor wafer, substrate, photomask, reticule, liquid crystal, etc.) by using an image. As shown in FIGS. 6, the automatic visual inspection apparatus 20 of the present invention has an image processor 9 for image processing the inspection image of the object to be inspected inputted from the external image input apparatus 1 such as an image pickup camera and comparing it with the reference image.

The image processor 9 has an image differential unit 2, an image division unit 3, a pixel precision position alignment unit 4, a function fitting unit 5, a sub-pixel precision position displacement calculating unit 6, an adjusted differential image forming unit 7, and an image comparison unit 8.

The image differential unit 2 takes one of the two images to be compared inputted from the external image input device 1 to be an inspection image which should be an objective image of the object to be inspected, and the other to be a reference image which should be compared with the inspection image. Each image is provided spatially with differentiation to form a differential image.

The image division unit 3 divides the differential image according to the predetermined number of divisions and size of the overlapping part with the adjacent image and forms the divisional differential image.

The pixel precision position alignment unit 4 carries out position alignment in the pixel size precision or pixel precision between the inspection image and the reference image in the unit of the divisional differential image to lay together the inspection image and the reference image.

The function fitting unit 5 regards the point at which the absolute pixel value is larger than the predetermined threshold value to be an edge in each divisional differential image, obtains a direction of the edge, obtains an intensity profile of the absolute value in respect to the direction orthogonal with the edge, applies to fit the predetermined single peak function to it, and obtains the maximum value point which is a coordinate of the point at which the function takes the maximum value in a sub-pixel precision which is a precision lower than the pixel size to take it as a coordinate for the edge.

The sub-pixel precision position displacement computing unit 6, after the overlaying of the images together in the pixel precision position alignment unit 4, takes that, with respect to a certain edge on the inspection image, if there is an edge in the region on a reference image corresponding to the neighborhood of the edge, these two edges are in corresponding relations, by which the difference of the mutual edge positions is regarded to be the displacement of the position in sub-pixel precision, so that the average value of the position displacement in sub-pixel precision of the whole edges in one divisional differential image is computed as a position displacement in sub-pixel precision.

The adjusted differential image forming unit 7 forms an adjusted differential image on the two edges which have been set to correspond by rewriting the pixel value in conformity with the predetermined single peak function form for the concentration distribution of the pixel value in the direction orthogonal with the edge.

The image comparison unit 8 compares the positions of the differential images by overlaying them in a sub-pixel precision based on the position displacement of the divisional differential image in sub-pixel precision, and in a case that there is a point which exceeds the predetermined threshold value in the difference, such point is regarded to be the defect of the object under inspection.

To the automatic visual inspection apparatus 20 of the present invention there are connected a parameter input apparatus 10 including a keyboard, ten-key, mouse, etc. for setting the number of divisions for dividing the image, threshold value, etc., an output apparatus 11 including a display, a printer, etc. for displaying the images, defective spot, etc., and a memory unit 12 for memorizing various kinds of data.

Next, the operation of the automatic visual inspection apparatus 20 of the present invention is illustrated.

Firstly, the image differential unit 2 sets one of the two inputted images from the image input apparatus 1 to be an inspection image, and the other to be a reference image, and by convoluting for example a SOBEL filter in each image, the respective differential images in vertical and horizontal directions are formed as the vertical differential image and horizontal differential image, thereby forming the total differential image having the square root of the sum of the square of each pixel value in the vertical and horizontal differential images.

Figure 8A:
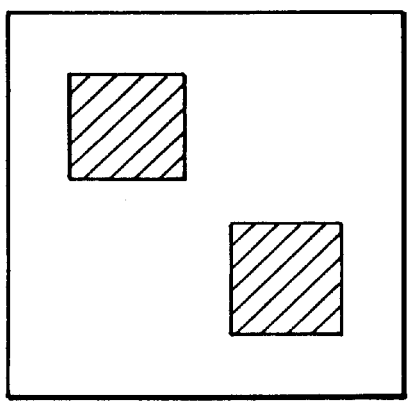
FIG. 8A is an illustrative view showing an input image.
Figure 8B:
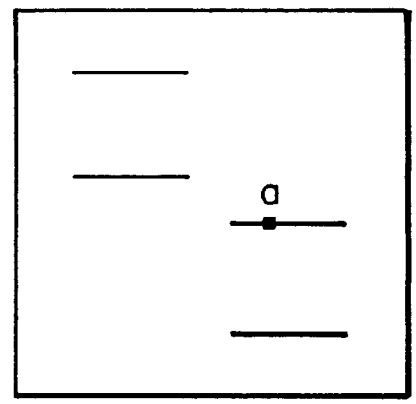
FIG. 8B is an illustrative view showing a vertical differential image.
Figure 8C:
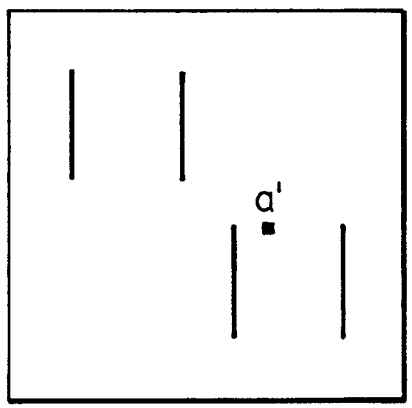
FIG. 8C is an illustrative view showing a horizontal differential image.
Figure 9A:
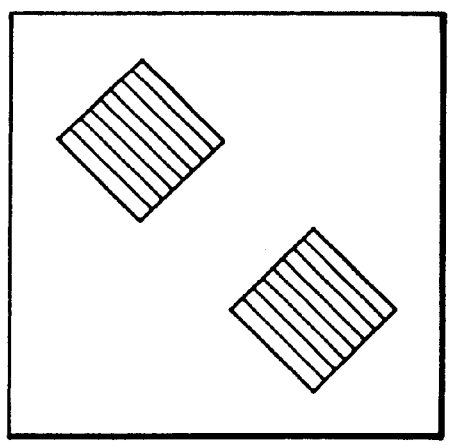
FIG. 9A is an illustrative view showing an input image.
Figure 9B:
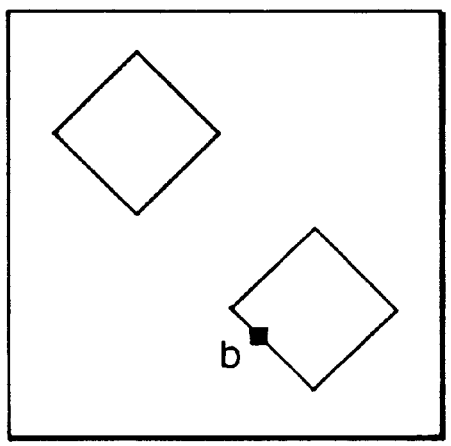
FIG. 9B is an illustrative view showing a vertical differential image.
Figure 9C:
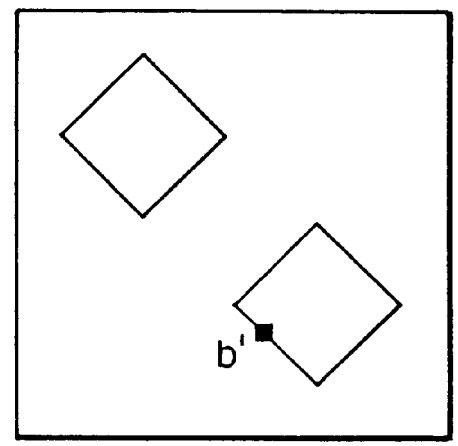
FIG. 9C is an illustrative view showing a horizontal differential image.

For example, when an image as shown in FIG. 8A is inputted, by carrying out vertical differentiation a horizontal edge is obtained as shown in FIG. 8B, and by carrying out horizontal differentiation a vertical edge is obtained as shown in FIG. 8C. Also, in a case that an image as shown in FIG. 9A is inputted, by carrying out vertical differentiation a slanting edge as shown in FIG. 9B is obtained, and by carrying out horizontal differentiation a slanting edge as shown in FIG. 9C is obtained.

Next, the image division unit 3 divides the vertical and horizontal differential image and the total differential image according to the predetermined number of divisions and the size of the overlaying of images with the adjacent image to make the respective images into divisional vertical differential image, divisional horizontal differential image, and divisional total differential image. The division of image is of course exchangeable with the image differentiation such that at first the input image may be divided by the image division unit 3 and differentiated by the image differentiation unit 2 to form a divisional vertical differential image, a divisional horizontal differential image, and a divisional total differential image.

Next, the pixel precision position alignment unit 4 effects overlaying of the inspection image and the reference image by performing position setting in pixel size precision by carrying out for example a template matting between the inspection image and the reference image on each divisional total differential image.

Next, the function fitting unit 5 regards the pixel in which the absolute pixel value of the divisional total differential image and the pixel values of the respective divisional vertical differential images are larger than the predetermined threshold value to be an edge in each divisional vertical differential image, obtains an intensity profile of the absolute pixel value in the vertical direction to the horizontal edge appearing on the divisional vertical differential image, applies to fit the predetermined single peak function to it, and obtains the maximum value point which is a coordinate of the point at which the function takes the maximum value in a sub-pixel precision which is a precision lower than the pixel size to take it as a vertical direction coordinate for the edge.

With respect to the divisional horizontal differential image, a single peak function is fitted to the vertical edge appearing on the divisional vertical differential image, and the maximum value point is obtained in a sub-pixel precision, which is taken as a horizontal direction coordinate for the edge.

Figure 8D:
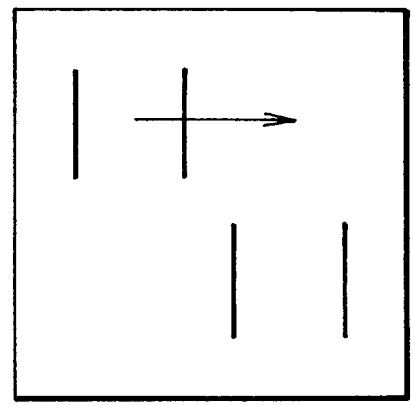
FIG. 8D is an illustrative view showing the function fitting in the horizontal direction to the vertical edge.

For example, when a horizontal differentiation is applied to the input image as shown in FIG. 8A and a vertical edge as shown in FIG. 8D is obtained, a function fitting is carried out to the vertical edge in the horizontal direction (arrow mark direction).

Figure 14:
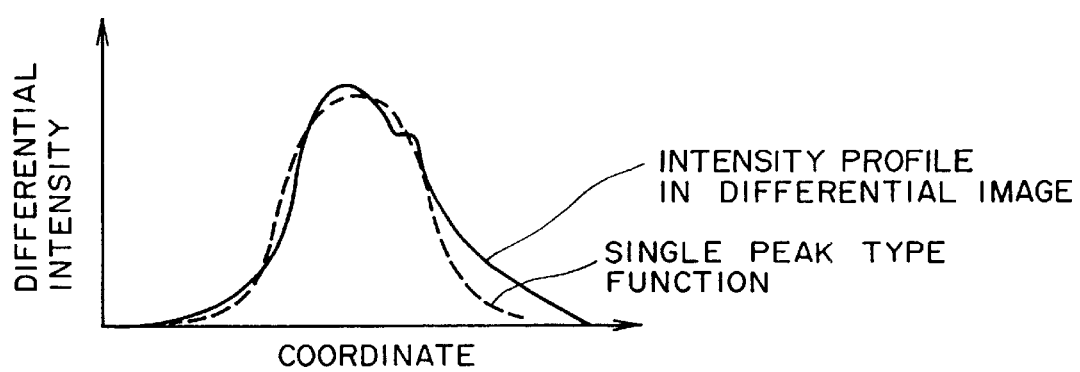
FIG. 14 is a graph showing the variation of the intensity of the coordinates wherein the ordinate is a coordinate, and the abscissa is a differential intensity, and a function of a single peak property in the differential image.

Intensity of the horizontal differential image (an absolute value of the horizontal differential intensity of the input image) becomes, in the neighborhood of the zone in which an edge is present, as shown in FIG. 14. To it, a single peak type function is fitted. Here, by the term of single peak type function is meant, as shown in FIG. 14, a function which is convex on a point on which the point to take the maximum value is only one. Also, the fitting procedure includes a least square method as a representative one, but the method is not limited to it. With respect to the case of the vertical differential image, the direction of differentiation, the direction of the edge, and the direction of the function fitting become all vertical to the case of the horizontal differential image, but basically the function fitting is carried out in the similar manner.

The sub-pixel precision position displacement computing unit 6, after the overlaying of the images together in the pixel precision position alignment unit 4, takes that, with respect to a certain edge on the divisional vertical differential image of the inspection image, if there is an edge on the same coordinate on the divisional horizontal differential image of the inspection image, then the edge is regarded to be a horizontal edge, and if there is an edge in the region on the divisional vertical differential image of the corresponding reference image in the vicinity of the edge on the divisional vertical differential image of the inspection image, such two edges are regarded to be in corresponding relations, by which the difference of the mutual edge positions is regarded to be the displacement of the position in sub-pixel precision.

If, on certain edge on the divisional horizontal differential image of an inspection image, there is no edge in the same coordinate on the divisional vertical differential image of the inspection image, the the edge is regarded to be a vertical edge, to which the same operation as in the case of the horizontal edge is applied to obtain position displacement in sub-pixel precision in the horizontal direction of the vertical edge in the corresponding relations. If, with respect to certain edge on the divisional vertical differential image of the inspection image, there is also an edge on the same coordinate on the divisional horizontal differential image of the inspection image, the edge is regarded to be a slanting edge.

For example, in a case of the input image as shown in FIG. 8A, with respect to the point which includes a horizontal edge on a vertical differential divisional image shown in FIG. 8B, namely, on the portion in which the vertical differential precision is strong, e.g., on the point a, the corresponding point a' is viewed by a horizontal differential image as shown in FIG. 8C, the horizontal differential intensity is not strong, without having an edge. That is to say, if, on the point a having the strong differential intensity in the vertical differential image, the differential intensity of the point on the horizontal differential image corresponding thereto is weak, the point a can be concluded as a point which constitutes a horizontal edge. Similarly, with respect to the point having strong differential intensity in the horizontal differential image, if the differential intensity of the point on the vertical differential image corresponding thereto is weak, then the point can be concluded as being a point which constitutes a vertical edge.

In the case of the input image as shown in FIG. 9A, the shapes of the edges on the vertical differential image as shown in FIG. 9B and on the horizontal differential image as shown in FIG. 9C are similar to each other. However, the pixel values of the respective images (i.e., the differential intensity of vertical differentiation and the differential intensity of horizontal differentiation) generally take the different values. Here, observing the point b having the strong vertical differential intensity on the vertical differential image as shown in FIG. 9B, the horizontal differentiation intensity of the point b' on the horizontal differential image as shown in FIG. 9C corresponding to the point is strong (the value is larger than the threshold value). Namely, if, with respect to a certain point having strong differential intensity on a vertical differential image, the horizontal differential intensity on a horizontal differential image corresponding thereto is strong, such point can be concluded as being a point to constitute a slanting edge.

If there is an edge in a region on a divisional vertical differential image of a reference image corresponding to the neighborhood of the edge of the divisional vertical differential image of the inspection image, or there is an edge in a region on a divisional horizontal differential image of a reference image corresponding to the nearest part of the edge of the divisional horizontal differential image of the inspection image, then these two edges are regarded to be in corresponding relations, and the difference of the mutual edge positions is taken as a position displacement in sub-pixel components in the direction orthogonal with the edge of mutual edges, and the position displacement is decomposed into the vertical direction component and the horizontal direction component.

With respect to the position displacement in sub-pixel precision of whole edges in a divisional vertical differential image and a divisional horizontal differential image corresponding thereto, average values of the respective components in the horizontal direction and in the vertical direction are obtained, respectively, and they are taken as the vertical directional position displacement and the horizontal directional position displacement of the sub-pixel precision of the respective divisional total differential image.

Figure 10A:
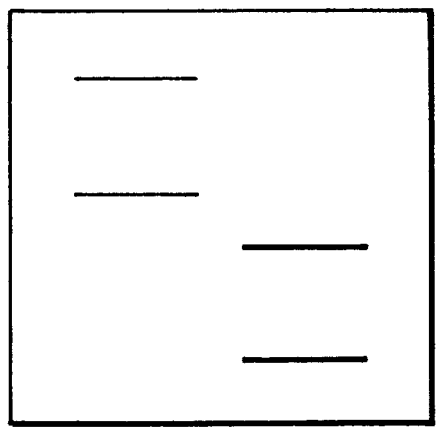
FIG. 10A is an illustrative view showing a vertical differential image of the inspection image.
Figure 10B:
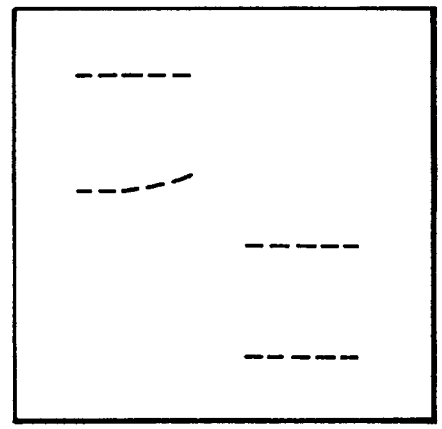
FIG. 10B is an illustrative view showing a vertical differential image of the reference image.
Figure 10C:
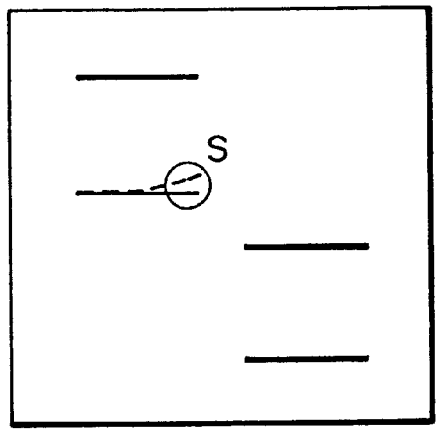
FIG. 10C is an illustrative view showing the condition where the vertical differential image of the inspection image and the vertical differential image of the reference image are mutually position aligned in pixel precision.
Figure 10D:
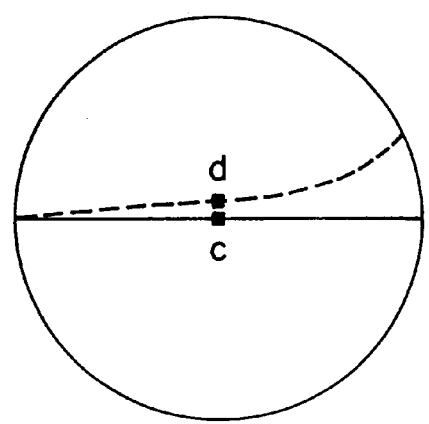
FIG. 10D is an enlarged view of the part S in 10C.

For example, when the vertical differential image of the inspection image as shown in FIG. 10A and the vertical differential image of the reference image as shown in FIG. 10B are subjected to position alignment in a pixel precision, the result becomes as shown in FIG. 10C. FIG. 10D is an enlarged view in which the part S in FIG. 10C is enlarged. As shown in FIG. 10D, with respect to the point c having the large vertical differential intensity on the vertical differential image of the inspection image, the points having large intensity of vertical differential intensity are searched on the vertical differential image of the reference image in the vicinity of the point on a reference image, and if a plurality of such points have been detected, the point d which is nearest to the point c out of them is regarded to be the point corresponding to the point c. Both the coordinate of the point c and the coordinate of the point d are determined by the sub-pixel precision in the vertical direction, and when the difference of these positions is to be taken as the size of the position displacement of the two images, the position displacement of the two edges is to be determined by the sub-pixel precision. Such operation is obtained on all the points having strong vertical differential intensity on the subject image, an average value of the position displacements in sub-pixel precision is obtained, which is to be taken finally as a position displacement of the sub-pixel precision in vertical direction of the two images.

Figure 11A:
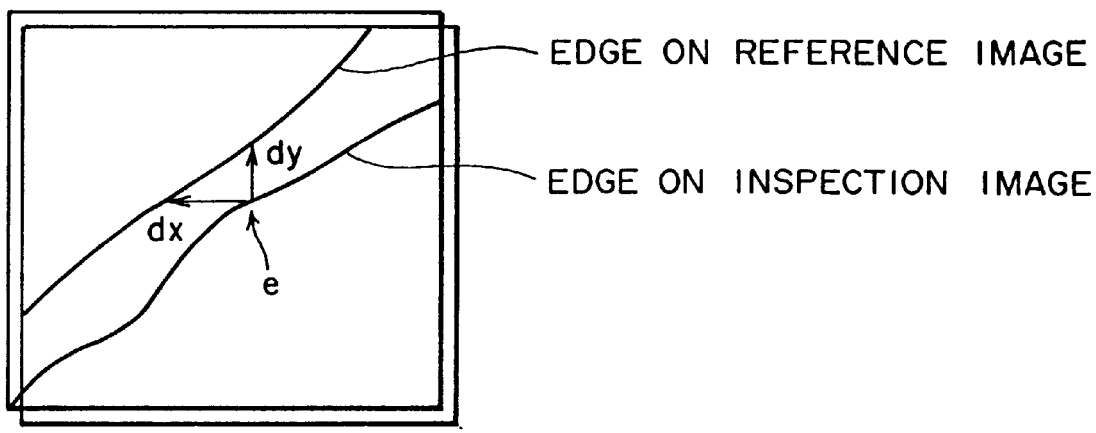
FIG. 11A is an illustrative view showing the positional displacement between the edge on the inspection image and the edge on the reference image.
Figure 11B:
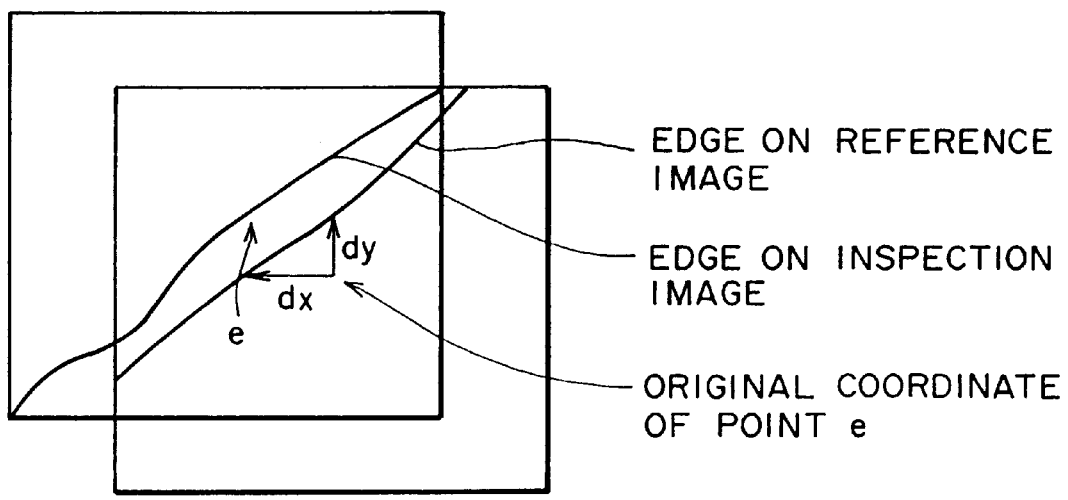
FIG. 11B is an illustrative view showing the condition of the inspection image displaced horizontally by dx, and vertically by dy.

In the case of the vertical edge, a position displacement of the sub-pixel precision in the horizontal direction is obtained in the same manner. In the case of the slanting edge, similarly, the position displacements of the reference image and the inspection image are obtained in the unit of the vertical differential image and the horizontal differential image. However, as shown in FIG. 11A, assuming the horizontal position displacement to be dx and the vertical position displacement to be dy, it does not follow that the dx and dy become in straight manner the position displacements of the inspection image and the reference image. If, as shown in FIG. 11B, the inspection image is shifted by dx horizontally, and dy vertically, then excessive displacements occur.

Figure 12A:
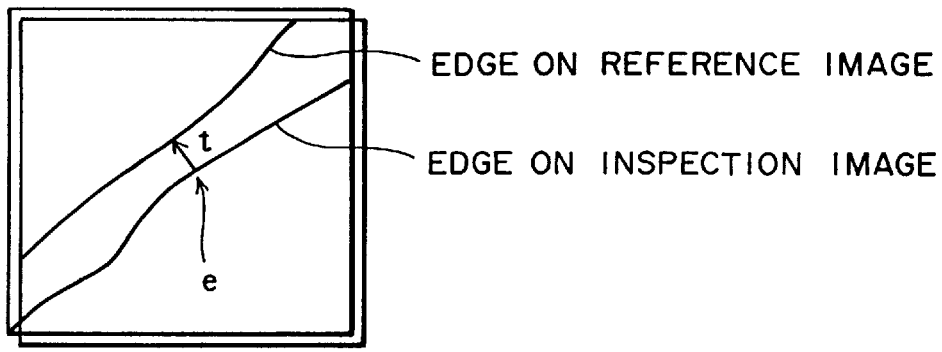
FIG. 12A is an illustrative view showing the positional displacement between the edge on the inspection image and the edge on the reference image.
Figure 12B:
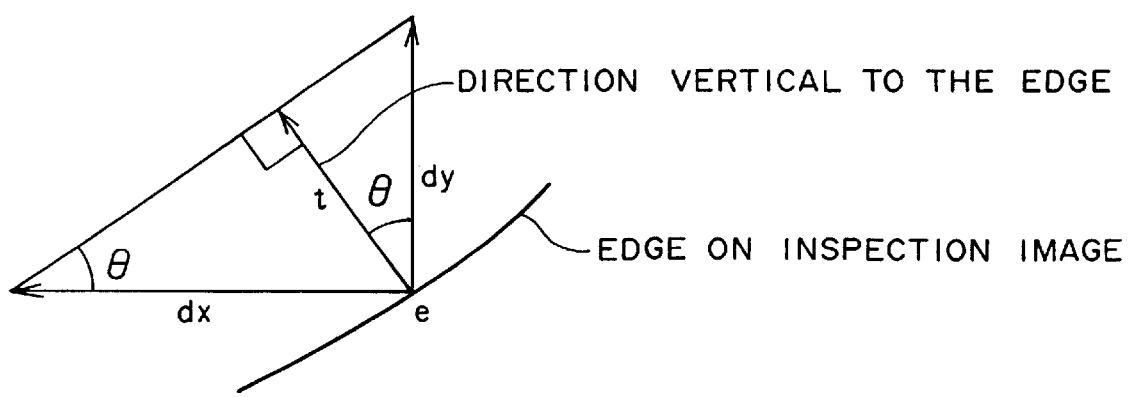
FIG. 12B is an enlarged view made by enlarging the area near the pointe in 12A.
Figure 12C:
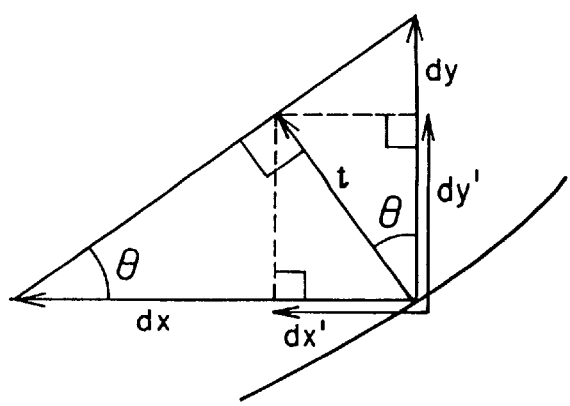
FIG. 12C is an illustrative view showing the true horizontal position displacement dx' and the true vertical position displacement dy'.

Accordingly, assuming that, as shown in FIG. 12A, the position displacement of the point e shown in FIG. 11A is in the direction vertical to the edge, the position displacement t in the vertical direction of the edge is obtained from dx and dy. The drawing which shows the zone near the point e by enlargement is FIG. 12B. The following expression 1 is obtainable from FIG. 12B.

$$t^2 = 1/(1/dx^2 + 1/dy^2) \tag{1}$$

where, $\tan\theta = dy/dx$.

The true position displacement in the horizontal direction dx' and the true position displacement in the vertical direction dy' to be obtained are obtainable by substituting the expression 1 into the following expression 2.

$$dx' = t\sin\theta = t^2/dx$$

$$dy' = t\cos\theta = t^2/dy \qquad (2)$$

Next, the adjusted differential image formation unit 7 forms an adjusted divisional vertical differential image by rewriting the pixel value so that the intensity profile in vertical direction conforms to the predetermined same single peak type function shape on two horizontal edges which have been correspondingly related on the divisional vertical differential image of the inspection image and the divisional vertical differential image of the reference image. With respect to the divisional horizontal differential image, an adjusted divisional horizontal differential image is formed by similarly rewriting the pixel value so that the intensity profile in horizontal direction of the vertical edge conforms to the predetermined same single peak type function shape. And, an adjusted divisional total differential image having as a pixel a square root of the square sum of the pixel values of the adjusted divisional vertical differential image and the adjusted divisional horizontal differential image is obtained.

Next, the image comparison unit 8 forms an adjusted divisional total differential image having position displacement by a sub-pixel by interpolating the intensity between the pixels in an adjusted divisional total differential image of either the inspection image or the reference image based on the position displacement of sub-pixel precision in each direction of vertical and horizontal in each divisional total differential image, overlays it with the other, and obtains for example an absolute value of the difference of the pixel values by the adjusted divisional total differential image of the inspection image and the adjusted divisional total differential image of the reference image, and in a case that there is found a point in which the obtained value exceeds the predetermined threshold value, such is regarded to be the defect. The coordinate of the defect spot is either displayed by an output device 11 or memorized in a memory device 12.

Next, the second embodiment of the present invention is described with reference to the drawings.

In the second embodiment, an image input apparatus 1, an image differential unit 2, an image division unit 3, a pixel precision position alignment unit 4, and an image comparison unit 8 show the same actions as those of the first embodiment.

In the second embodiment, the function fitting unit 5 regards the pixel of which the absolute value is larger than the predetermined threshold value to be an edge in each divisional differential image, taking, for example, an arctangent of the ratio of the pixel value of the vertical differential image to the horizontal differential pixel in the image differential unit 2 to be the direction of its edge, and obtains an intensity profile of the absolute value in respect to the direction orthogonal with the edge, then fits the predetermined single peak function to the obtained intensity profile, and obtains the maximum value point which is a coordinate of the point at which the function takes the maximum value in a sub-pixel precision which is a precision lower than the pixel size to take it as a coordinate for the edge.

Figure 13A:
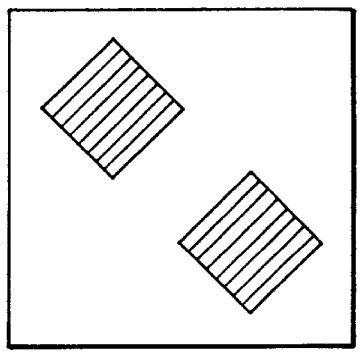
FIG. 13A is an illustrative view showing an input image.
Figure 13B:
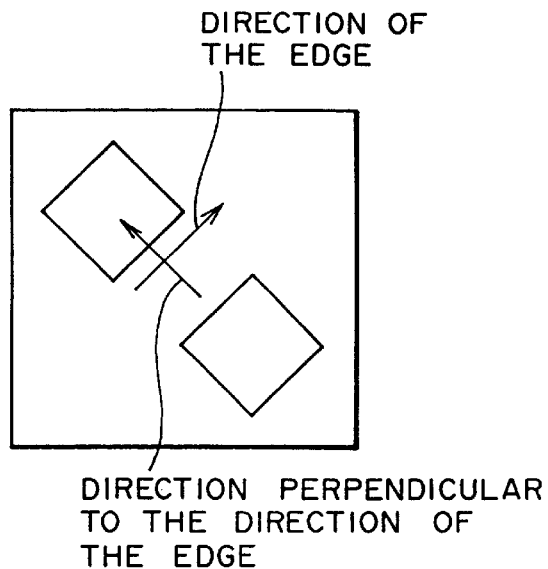
FIG. 13B is an illustrative view showing the total differential image obtained by adding a square of the vertical differential image and a square of the horizontal differential image, and taking the square root thereof.

For example, by an existing procedure using SOBEL filter, the direction of the edge is obtained from the vertical differential image and the horizontal differential image of the input image shown in FIG. 13A (ref. FIG. 13B). FIG. 13B shows a total differential image obtained by adding the square of the vertical differential image and the square of the horizontal differential image and obtaining the square root thereof. And, an intensity profile is obtained in the direction orthogonal with the obtained edge direction, to which function fitting is performed with a single peak type function (ref. FIG. 14) to obtain the edge position.

Also, in the second embodiment, the sub-pixel precision position displacement computing unit 6 takes for example the portion in which the curvature of the edge is larger than the predetermined threshold value in the divisional total differential image to be a corner, and if a corner exists, after overlaying the images together in the pixel precision position alignment unit 4, takes that, with respect to a certain corner on the inspection image, if there is a corner in the region on a reference image corresponding to the neighborhood of the corner, these two corners are in corresponding relations, by which the difference of the mutual corner positions is regarded to be the displacement of the position in sub-pixel precision, the position displacement is separated into the vertical direction and the horizontal direction, so that the average value of the position displacement in sub-pixel precision of the whole corners in one divisional total differential image is obtained independently on vertical and horizontal directions, and they are taken as position displacements in sub-pixel precision of the divisional total differential image.

Also, the edges adjacent to the corners in the corresponding relations on the two images are regarded to be in the corresponding relations.

Figure 16A:
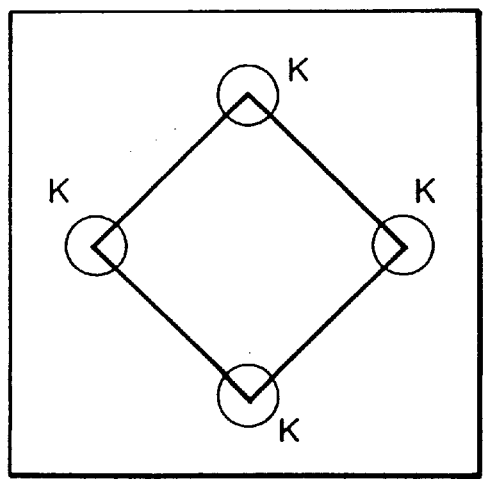
FIGS. 16A and 16B are illustrative views for illustrating the position alignment using a corner; and 16B is an enlarged view of the corner K.
Figure 16B:
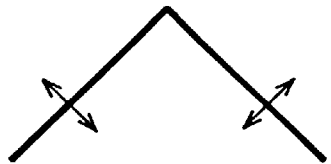

For example, as shown in FIG. 16A, a corner K is detected by a conventional procedure such as to take the point at which the curvature variation of the edge is large to be the corner. Since the corner position has been obtained by the sub-pixel precision, as shown in FIG. 16B, the coordinate of the corner which is a crossing point of the two edges having different directions is also determined by the sub-pixel precision in the arrow mark direction. After the position alignment in pixel precision between the inspection image and the reference image, the corners near to each other are set to be the corners in corresponding relations, and the position displacement between the images is obtained from the difference of the positions of the corners in corresponding relations.

If no corner exists on the divisional total differential image, with respect to a certain edge on the inspection image, and if an edge exists in the region on the reference image corresponding to the nearest part of the edge, then these two edges are regarded to be in the corresponding relations, by which the difference of the mutual edge positions is set to be the position displacement in sub-pixel precision on the direction orthogonal with the mutual edges, the position displacement is decomposed in vertical direction and horizontal direction, an average value of the position displacements in sub-pixel precision of the whole edges in one divisional total differential image is obtained individually with respect to the vertical and horizontal directions, and the resultant values are taken as the position displacements of the divisional total differential image in sub-pixel precision.

In the first embodiment, the direction of the position displacements of the mutual slanting edges is supposed to be the direction orthogonal with the edge. Because of this, in a case that the edges are not in the orthogonal direction, no coordination can be made and there is a possibility to make erroneous position alignment. On the other hand, in the second embodiment, since the position alignment is effected at the corner part, as far as the corner exists, even when the displacements of mutual slanting edges are in the direction not orthogonal with the edge position alignment can be made more accurately.

However, in the second embodiment, with respect to the slanting edge in an optional direction, the change in the intensity on the divisional total differential image in the direction orthogonal with said edge is required to be obtained by interpolating the intensity between the pixels. Further, the direction of the edge is required to be obtained on each pixel.

Figure 15A:
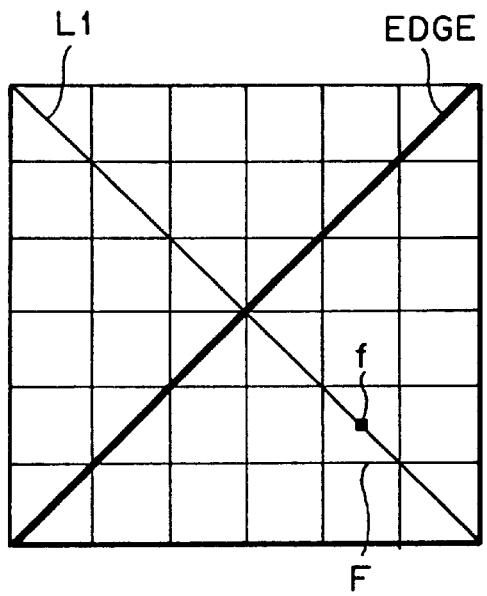
FIGS. 15A and 15B are illustrative views illustrating the case of interpolating the intensity between the pixels to obtain the distribution of concentrations in a direction orthogonal with the edge.
Figure 15B:
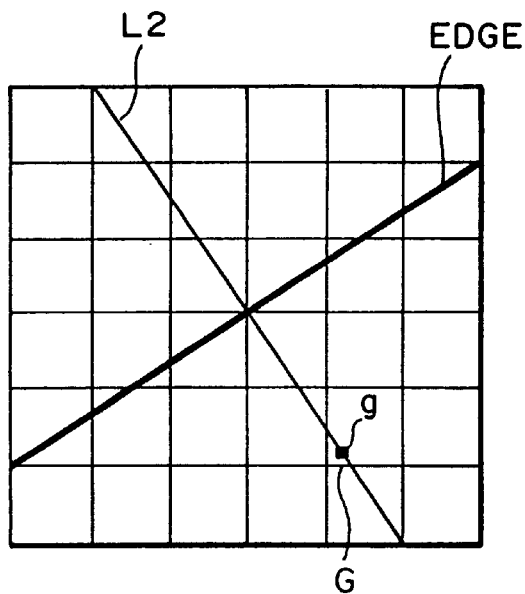

For example, in a case that the slanting edge has an angle of 45 degrees as shown in FIG. 15A, the line L1 drawn in the direction vertical to it necessarily passes through the center of each pixel value. The point f on the line L1 fully agrees with the center of the pixel F, and the pixel value of the pixel F can be regarded as the intensity on the line L1. However, as shown in FIG. 15B, in a case that the edge is not vertical nor horizontal nor 45 degrees, the straight line drawn vertical to the edge does not necessarily pass through the center of each pixel. Here, assuming the straight line drawn in a direction vertical to the edge of FIG. 15B to be L2, in a case that the line L2 passes through the pixel G, the point g on the line L2 does not agree with the center of the pixel G. Consequently, the pixel value of the pixel G cannot be regarded as the intensity of the point g on the line L2. Therefore, based on the pixel value of the pixel in the periphery of the pixel G, the intensity of the point g is obtained by relative interpolation method or the like.

Accordingly, in a case of reducing the calculation amount, the first embodiment is preferable.

It may be practical to apply first the first embodiment, and then the second embodiment only to the image on which the defect of the object to be inspected has been found. Even in a case that the defect found by the first embodiment is a false defect caused by the wrong position setting, it can be made clear by the second embodiment which has a higher precision of position alignment that there is no difference between the inspection image and the reference image, and that the defect detected by the first embodiment is a false defect. When the pixels containing defects are less in comparison with the inspection image, the method of applying the second embodiment only to a part of the images requires less calculation amount than the case of applying the second embodiment to the whole inspection images.

Figure 1A:
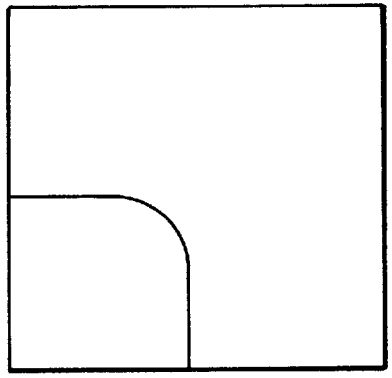
FIGS. 1A through 1D are illustrative views for explaining an example of false defect detection at the edge portion in the vicinity of the corner, in the conventional method.
Figure 1B:
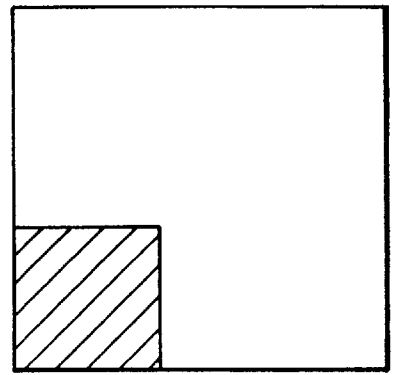
Figure 1C:
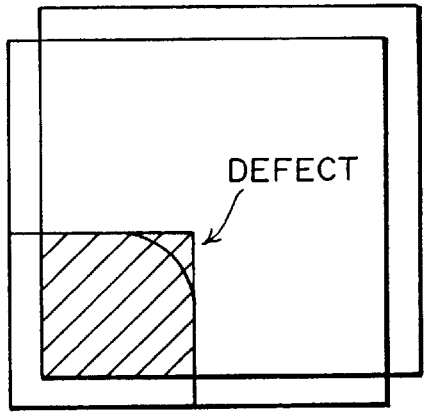
Figure 1D:
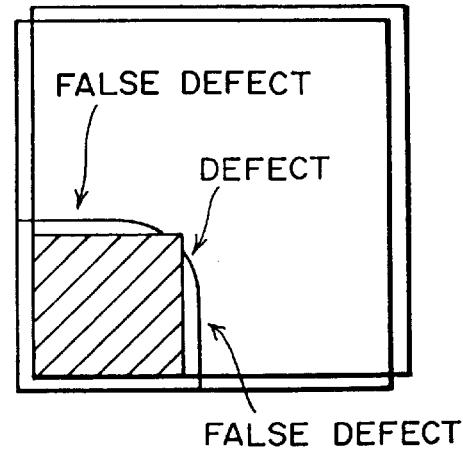
Figure 2A:
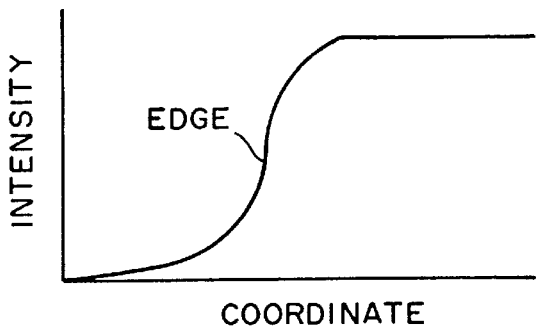
FIGS. 2A through 2C are graphs for explaining an example for detecting the false defect in the case where the intensity gradients in the portions near the edge differ between the images to be compared, in the conventional procedures.
Figure 2B:
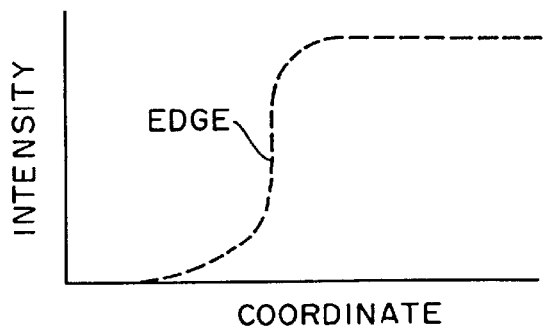
Figure 2C:
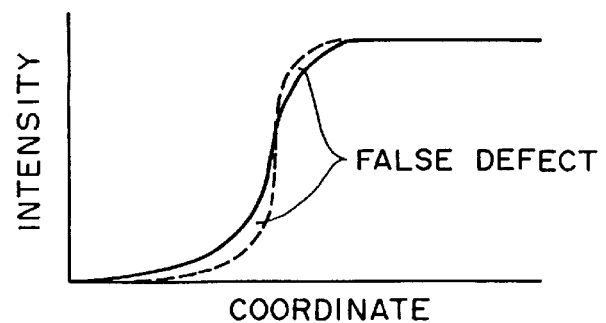
Figure 3A:
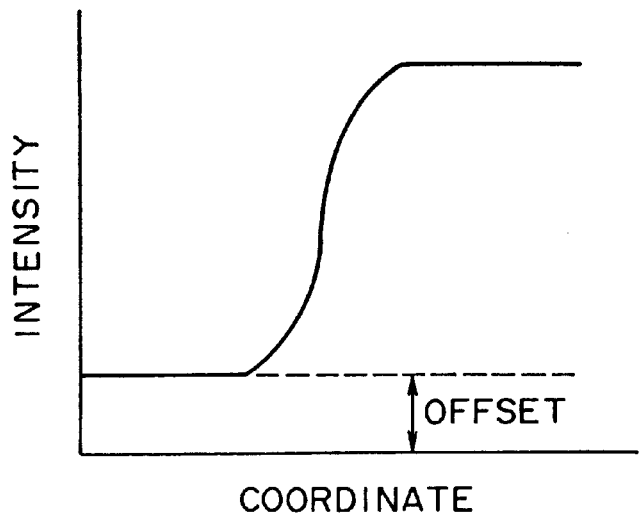
FIGS. 3A and 3B are graphs for illustrating an example of the false defect detection in the case of the difference of the offsets between the images to be compared, in the conventional method.
Figure 3B:
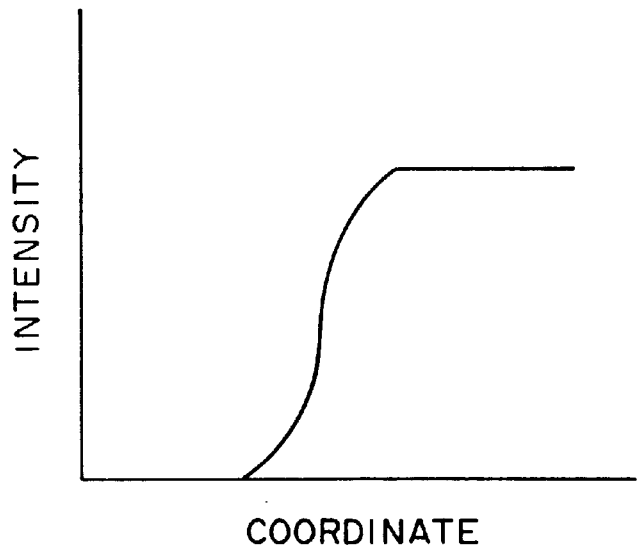
Figure 4A:
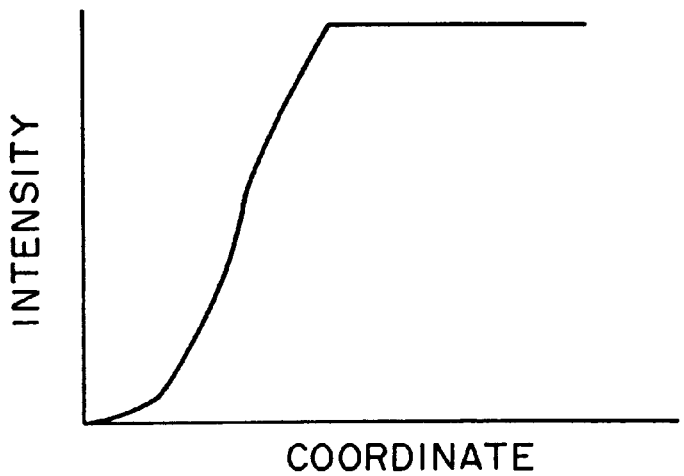
FIGS. 4A and 4B are graphs for illustrating an example of the false defect detection in the case of the difference in the gain of the detectors or in the intensity of the illumination, between the images to be compared, in the conventional method.
Figure 4B:
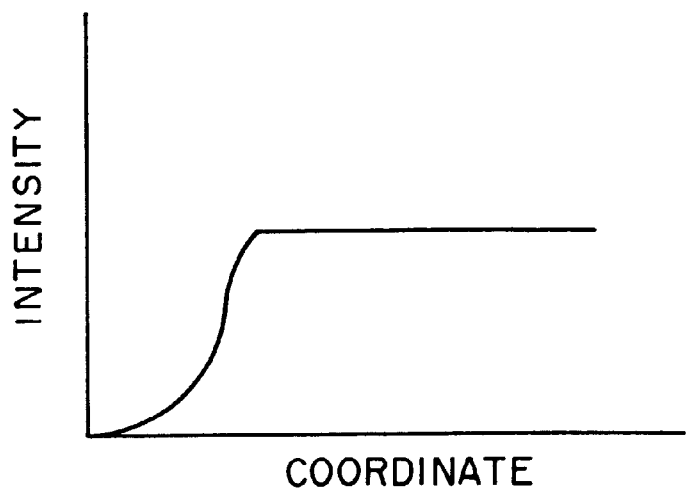
Figure 7:
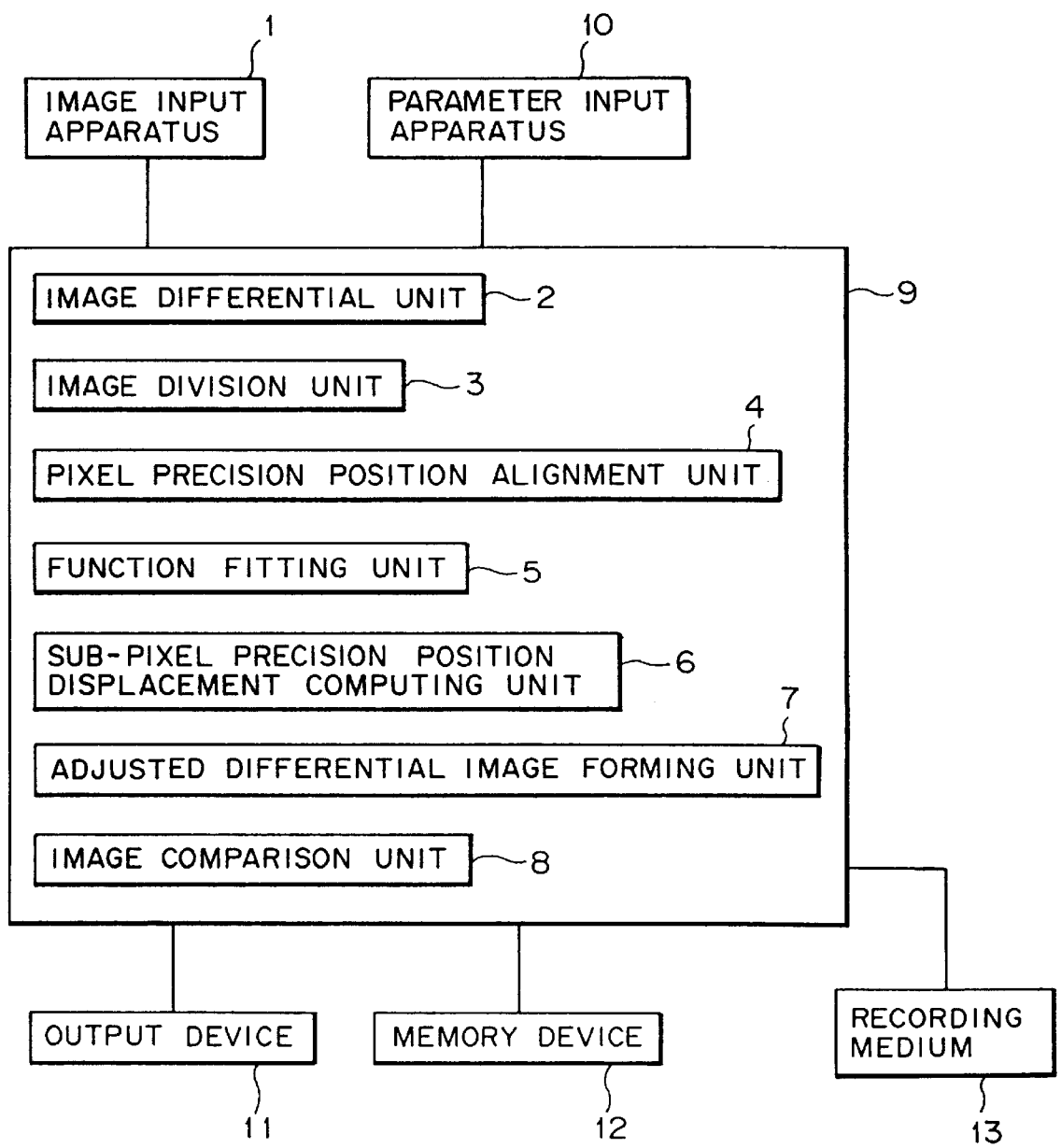
FIG. 7 is a block diagram showing the constitution of the third embodiment of the present invention.

FIG. 2 is a block diagram showing the constitution of the third embodiment of the present invention. As shown in FIG. 7, the third embodiment of the present invention has a recording medium 13 which records a program (automatic visual inspection program) for causing a computer to execute the image differential processing by the image differentiation unit 2, an image divisional processing by the image division unit 3, a pixel precision position aligning processing by the pixel precision position aligning unit 4, a function fitting processing by the function fitting unit 5, a sub-pixel precision position displacement computation processing by the sub-pixel precision position displacement computation unit 6, an adjusted differential image forming processing by the adjusted differential image forming unit 7, and an image comparison processing by the image comparison unit 8, as illustrated above. The recording medium 13 may be a magnetic disk, a CD-ROM, a semiconductor memory or other recording medium.

The above automatic visual inspection program is read into the image processing unit 9 from the recording medium 13, and the image processing unit 9 executes processing according to the automatic visual inspection program.

According to the present invention, because of the position alignment made between the edges, even when defects exist in the corner portion, false defect is less caused to occur on the edge portion in the vicinity of such corner portion.

Further, in the differential images to be compared, the intensity profile of the corresponding edge portions are modified into the same shape, so that even if the intensity gradients in the vicinity of the edges differ between the images to be compared, false defect is less caused to occur.

Moreover, since the offset which is a DC component in image is lost by differentiation, false defect is less caused to occur even when the offsets differ between the images to be compared.

Furthermore, since the intensity profile of the corresponding edge portions is modified into the same shape, even if the gains of the detector or the intensity of illumination differ between the images to be compared, false defects are less caused to occur.

Figure 5A:
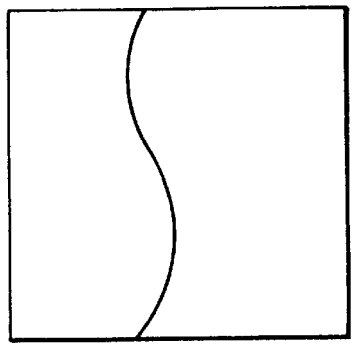
FIGS. 5A through 5C are illustrative views for illustrating the case where, even if the edge positions are different by about a sub-pixel, there may be cases where the difference occurs by 1 pixel on the edge image.
Figure 5B:
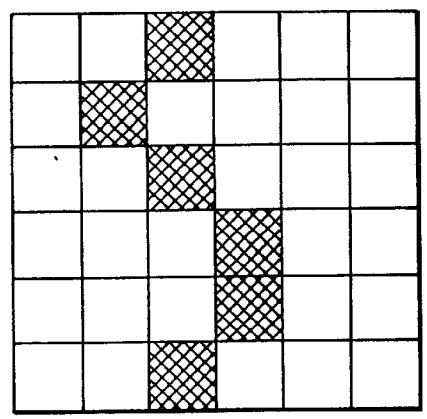
Figure 5C:
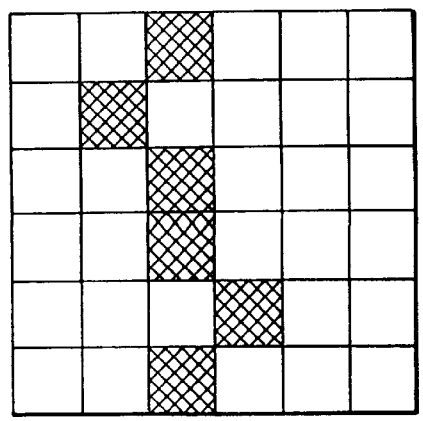

Also, in a case of comparing the edge images as shown in FIG. 5A, even if the real edge positions differ by about the sub-pixel as shown in FIGS. 5B and 5C, the difference on the edge image by a conventional method becomes that of one pixel to become the cause for the false defect. Here, FIG. 5A shows an edge image having the infinite resolution; FIG. 5B shows an edge image in which the edge image of FIG. 5A is expressed by the image of 6×6 in pixel number; and FIG. 5C shows an edge image having the infinite resolution in which the edge position is displaced by a sub-pixel by noise expressed by the image of 6×6 in pixel number. However, in a case of comparing the edge profile of the modified images following the single peak function form as in the present invention, even if the edge positions of the sub-pixels differ, due to the small difference of the pixel values, false defect is less caused to occur.

As reviewed above, since in the present invention generation of the false defects can be prevented, highly reliable automatic visual inspection can be carried out.

In the present invention, due to the computation of the position displacement of the sub-pixel precision on each divisional differential image by obtaining the distance of the corresponding edges between the images to be compared, there is no necessity to make comparison by forming magnified images. Accordingly, even if the precision of position alignment is elevated, no increase in the necessary calculation amount or memory capacity should occur.

The present invention is not limited to the above embodiments but can be subjected to various modifications within the scope of the technical matters described in the claim. For example, the data of the reference image may be processed by reading out from the memory device 12 such as a memory to an image processing unit 9.

What is claimed is:

1. An automatic visual inspection apparatus comprising:
   an image division differential unit having inputs of an inspection image on the object to be inspected and a reference image for making comparison with the inspection image, for spatially differentiating the respective inputted images and dividing them into the predetermined number of divisions to form the divisional differential images;
   a pixel precision position alignment unit overlaying the inspection image and the reference image by carrying out the position alignment in pixel precision which is a pixel size precision between the inspection image and the reference image on each of the divisional differential image formed by said image division differential unit;

a function fitting unit which regards the point where the absolute pixel value is larger than the predetermined threshold value to be an edge in each divisional differential image, obtaining the direction of the edge, obtaining the intensity profile of the absolute pixel value in the direction orthogonal with the edge, fitting a predetermined single peak function to it, obtaining the maximum value point which is a coordinate of the point where its function takes the maximum value by a sub-pixel precision which is the precision lower than the pixel size, and employing the resulting value as coordinate of an edge;

a sub-pixel precision position displacement computing unit which functions so that, if, after the laying over of the images together in the pixel precision position aligning unit, there is an edge in the region on the reference image corresponding to the neighborhood of the edge, these two edges are regarded as being in the corresponding relations, and computing the difference of the mutual edge positions as a position displacement of the sub-pixel precision;

an adjusted differential image forming unit for forming the adjusted differential image by rewriting the pixel value so that the intensity profile of the pixel value in the direction orthogonal with the edge should follow the previously given single peak type function form on the corresponding two edges; and an image comparison unit for detecting the defect of the object to be inspected by comparing the adjusted divisional differential image of the inspected image with the adjusted divisional differential image of the reference image based on the position displacement of the sub-pixel precision of each divisional differential image computed by the sub-pixel precision position displacement computing unit.

2. The automatic visual inspection apparatus according to claim 1, wherein said sub-pixel precision position displacement computing unit compute the average value of the position displacement in sub-pixel precision in all edges in one divisional differential image as the position displacement of the sub-pixel precision of said divisional differential image.

3. The automatic visual inspection apparatus according to claim 1, wherein the image comparison unit obtain the absolute value of the pixel value by the adjusted divisional differential image of the inspection image and the adjusted divisional differential image of the reference image, and in a case that the resulting value exceeds the predetermined threshold value, the unit regard said result to be the defect of the object to be inspected.

4. The automatic visual inspection apparatus according to claim 1, wherein said image comparison unit form the adjusted divisional differential image having the position displacement by a sub-pixel by interpolating the intensity between the pixels in either one of the adjusted divisional differential image, and compares it with the other adjusted differential image.

5. The automatic visual inspection apparatus according to claim 1, wherein the sub-pixel precision position displacement computing unit detect a corner on the divisional differential image, and if a corner exists, the unit effect laying over the images in the pixel precision position alignment unit, after which, if, with respect to the certain corner on the inspected image, there is a corner in the region on the reference image corresponding to the nearest part to said corner, these two corners are regarded to be in corresponding relations, and the difference of the mutual corner positions is computed as the position displacement of the sub-pixel precision between the corners.

6. An automatic visual inspection method comprising the steps of:

inputting an inspection image on the object to be inspected and a reference image for making comparison with the inspection image, and generating a differentiated images by spatially differentiating the respective inputted images;

generating divisional differential images by dividing the differential images according to the predetermined number of divisions;

overlaying the inspection image and the reference image by carrying out the position alignment in pixel precision which is a pixel size precision between the inspection image and the reference image on each formed divisional differential image;

obtaining a coordinate of an edge, by regarding the point where the absolute pixel value is larger than the predetermined threshold value to be an edge in each divisional differential image, obtaining the direction of the edge, obtaining the intensity profile of the absolute pixel value in the direction perpendicular to the direction of the edge, fitting a predetermined single peak function to it, obtaining the maximum value point which is a coordinate of the point where its function takes the maximum value by a sub-pixel precision which is the precision lower than the pixel size and employing the resulting value as said coordinate of the edge;

regarding, after the mutual laying over of the images, if, on certain edge on the inspection image, there is an edge in the region on the reference image corresponding to the neighborhood of the edge, these two edges to be in the corresponding relations, and computing the difference of the mutual edge positions as a position displacement of the sub-pixel precision;

forming an adjusted differential image by rewriting the pixel value so that the intensity profile in the direction orthogonal with the edge should follow the previously given single peak type function form on the corresponding two edges;

detecting the defect of the object to be inspected by comparing the adjusted divisional differential image of the inspected image with the adjusted divisional differential image of the reference image based on the position displacement of the sub-pixel precision of each divisional differential image computed.

7. An automatic visual inspection method comprising the steps of:

inputting an inspection image on the object to be inspected and a reference image for comparison with said inspection image, and dividing the respective images according to the predetermined number of divisions;

spatially differentiating the divided image to form a divisional differential image;

overlaying an inspection image and a reference image by carrying out position alignment in pixel precision which is a pixel size precision between the inspection image and the reference image on each formed divisional differential image;

obtaining a coordinate of an edge, by regarding the point where the absolute pixel value is larger than the predetermined threshold value to be an edge in each divisional differential image, obtaining the direction of the edge, obtaining the intensity profile of the absolute pixel value in the direction perpendicular to the edge, fitting a predetermined single peak function to it, obtaining the maximum value point which is a coordinate of the point where its function takes the maximum value by a sub-pixel precision which is the precision lower than the pixel size, and employing the resulting value as the coordinate of the edge;

obtaining sub-pixel precision position displacement, by, after the laying over of the images together in the pixel precision position alignment step, if there is an edge in the region on the reference image corresponding to the neighborhood of the edge, these two edges are regarded as being in the corresponding relations, and computing the difference of the mutual edge positions as a position displacement of the sub-pixel precision;

forming an adjusted differential image by rewriting the pixel value so that the intensity profile of the pixel value in the direction orthogonal with the edge should follow the previously given single peak type function form on the corresponding two edges; and comparing the adjusted divisional differential image of the inspected image with the adjusted divisional differential image of the reference image based on the position displacement of the sub-pixel precision of each divisional differential image computed as above.

8. A recording medium having recorded a program for causing a computer to execute:

an image division differential processing having inputs of an inspection image on the object to be inspected and a reference image for making comparison with the inspection image, spatially differentiating the respective inputted images and dividing them into the, predetermined number of divisions to form the divisional differential images;

a pixel precision position alignment processing for laying the inspection image and the reference image together by carrying out the position alignment in pixel precision which is a pixel size precision between the inspection image and the reference image on each of the divisional differential image formed by the image division differential unit;

a function fitting processing so designed as to regard the point where the absolute pixel value is larger than the predetermined threshold value to be an edge in each divisional differential image, obtaining the direction of the edge, obtaining the intensity profile of the absolute pixel value in the direction orthogonal with the edge, fitting a predetermined single peak function to it, obtaining the maximum value point which is a coordinate of the point where its function takes the maximum value by a sub-pixel precision which is the precision lower than the pixel size, and employing the resulting value as coordinate of an edge;

a sub-pixel precision position displacement computing processing which functions so that, after the laying over of the images together in the pixel precision position alignment processing, if there is an edge in the region on the reference image corresponding to the neighborhood of the edge, these two edges are regarded as being in the corresponding relations, and computing the difference of the mutual edge positions as a position displacement of the sub-pixel precision;

an adjusted differential image formation processing for forming the adjusted differential image by rewriting the pixel value so that the intensity profile of the pixel value in the direction orthogonal with the edge should follow the previously given single peak type function form on the corresponding two edges; and an image comparison processing for detecting the defect of the object to be inspected by comparing the adjusted divisional differential image of the inspected image with the adjusted divisional differential image of the reference image based on the position displacement of the sub-pixel precision of each divisional differential image computed by the sub-pixel precision position displacement computing unit.

* * * * *